(12) United States Patent
Ludwin et al.

(10) Patent No.: US 8,979,772 B2
(45) Date of Patent: Mar. 17, 2015

(54) ZERO-DRIFT DETECTION AND CORRECTION IN CONTACT FORCE MEASUREMENTS

(75) Inventors: Doron Moshe Ludwin, Haifa (IL); Galia Givaty, Haifa (IL); Aharon Turgeman, Zichron Ya'acov (IL); Natan Katz, Kiryat Bialik (IL)

(73) Assignee: Biosense Webster (Israel), Ltd. (IL)

( * ) Notice: Subject to any disclaimer, the term of this patent is extended or adjusted under 35 U.S.C. 154(b) by 851 days.

(21) Appl. No.: 12/938,458

(22) Filed: Nov. 3, 2010

(65) Prior Publication Data

US 2012/0108988 A1     May 3, 2012

(51) Int. Cl.
*A61B 5/103*     (2006.01)
*A61B 18/14*     (2006.01)
*A61B 19/00*     (2006.01)
*A61B 18/00*     (2006.01)

(52) U.S. Cl.
CPC ....... *A61B 18/1492* (2013.01); *A61B 2019/465* (2013.01); *A61B 2019/464* (2013.01); *A61B 2019/5251* (2013.01); *A61B 2018/00357* (2013.01)
USPC .......................................... 600/587; 600/508

(58) Field of Classification Search
USPC ....................................................... 600/587
See application file for complete search history.

(56) References Cited

U.S. PATENT DOCUMENTS

| | | |
|---|---|---|
| 3,841,150 A | 10/1974 | Pearson |
| 3,971,364 A | 7/1976 | Fletcher et al. |
| 4,764,114 A | 8/1988 | Jeffcoat et al. |
| 4,856,993 A | 8/1989 | Maness et al. |
| 4,930,494 A | 6/1990 | Takehana et al. |
| 5,263,493 A | 11/1993 | Avitall |
| 5,368,564 A | 11/1994 | Savage |
| 5,391,199 A | 2/1995 | Ben-Haim |
| 5,462,527 A | 10/1995 | Stevens-Wright et al. |
| 5,487,757 A | 1/1996 | Truckai et al. |
| 5,499,542 A | 3/1996 | Morlan |
| 5,542,434 A | 8/1996 | Imran et al. |
| 5,558,091 A | 9/1996 | Acker et al. |
| 5,563,354 A | 10/1996 | Kropp |

(Continued)

FOREIGN PATENT DOCUMENTS

| | | |
|---|---|---|
| DE | 19750441 A | 6/1999 |
| EP | 928601 A1 | 7/1999 |

(Continued)

OTHER PUBLICATIONS

Biter, William J. et al., "Magnetic Wire Strain Sensor", 33rd International Sampe Technical Conference, Nov. 5-8, 2001, vol. 33, pp. 12-23, Seattle, WA.

(Continued)

*Primary Examiner* — Max Hindenburg
*Assistant Examiner* — Renee Danega (57) ABSTRACT

A method, consisting of inserting a probe having a force sensor into a body cavity of a patient, and receiving from the force sensor a plurality of measurements, each of the measurements indicative of a force applied to the force sensor. The method further includes detecting that the measurements received over a period of time of at least a specified duration have not varied by more than a predefined amount, and setting a baseline of the force sensor, for use in further measurements, to a value based on the measurements received during the period.

20 Claims, 3 Drawing Sheets

(56) References Cited

U.S. PATENT DOCUMENTS

| | | | |
|---|---|---|---|
| 5,662,124 A | 9/1997 | Wilk | |
| 5,673,695 A | 10/1997 | McGee et al. | |
| 5,680,860 A | 10/1997 | Imran | |
| 5,685,878 A | 11/1997 | Falwell et al. | |
| 5,728,149 A | 3/1998 | Laske et al. | |
| 5,769,843 A | 6/1998 | Abela et al. | |
| 5,826,576 A | 10/1998 | West | |
| 5,833,608 A | 11/1998 | Acker | |
| 5,836,894 A | 11/1998 | Sarvazyan | |
| 5,860,974 A | 1/1999 | Abele | |
| 5,861,024 A | 1/1999 | Rashidi | |
| 5,902,248 A | 5/1999 | Millar et al. | |
| 5,916,147 A | 6/1999 | Boury | |
| 5,944,022 A | 8/1999 | Nardella et al. | |
| 5,947,320 A | 9/1999 | Bordner et al. | |
| 5,964,757 A | 10/1999 | Ponzi | |
| 5,974,320 A | 10/1999 | Ward et al. | |
| 5,983,126 A | 11/1999 | Wittkampf | |
| 6,048,329 A | 4/2000 | Thompson et al. | |
| 6,063,022 A | 5/2000 | Ben Haim | |
| 6,123,699 A | 9/2000 | Webster, Jr. | |
| 6,171,277 B1 | 1/2001 | Ponzi | |
| 6,177,792 B1 | 1/2001 | Govari et al. | |
| 6,183,463 B1 | 2/2001 | Webster, Jr. | |
| 6,198,974 B1 | 3/2001 | Webster, Jr. | |
| 6,201,387 B1 | 3/2001 | Govari | |
| 6,203,493 B1 | 3/2001 | Ben Haim | |
| 6,216,027 B1 | 4/2001 | Willis et al. | |
| 6,226,542 B1 | 5/2001 | Reisfeld | |
| 6,239,724 B1 | 5/2001 | Doron et al. | |
| 6,241,724 B1 | 6/2001 | Fleischman et al. | |
| 6,266,551 B1 | 7/2001 | Osadchy et al. | |
| 6,272,371 B1 | 8/2001 | Shlomo | |
| 6,272,672 B1 | 8/2001 | Conway | |
| 6,301,496 B1 | 10/2001 | Reisfeld | |
| 6,332,089 B1 | 12/2001 | Acker et al. | |
| 6,334,837 B1 | 1/2002 | Hein | |
| 6,335,617 B1 | 1/2002 | Osadchy et al. | |
| 6,351,549 B1 | 2/2002 | Souluer | |
| 6,436,059 B1 | 8/2002 | Zanelli | |
| 6,456,864 B1 | 9/2002 | Swanson et al. | |
| 6,484,118 B1 | 11/2002 | Govari | |
| 6,551,302 B1 | 4/2003 | Rosinko et al. | |
| 6,569,098 B2 | 5/2003 | Kawchuk | |
| 6,574,492 B1 | 6/2003 | Ben Haim et al. | |
| 6,584,856 B1 | 7/2003 | Biter et al. | |
| 6,602,242 B1 | 8/2003 | Fung et al. | |
| 6,612,992 B1 | 9/2003 | Hossack et al. | |
| 6,618,612 B1 | 9/2003 | Acker et al. | |
| 6,690,963 B2 | 2/2004 | Ben-Haim et al. | |
| 6,695,808 B2 | 2/2004 | Tom | |
| 6,711,429 B1 | 3/2004 | Gilboa et al. | |
| 6,727,371 B2 | 4/2004 | Müller et al. | |
| 6,814,733 B2 | 11/2004 | Schwartz et al. | |
| 6,835,173 B2 | 12/2004 | Couvillon, Jr. | |
| 6,892,091 B1 | 5/2005 | Ben Haim et al. | |
| 6,915,149 B2 | 7/2005 | Ben Haim | |
| 6,945,956 B2 | 9/2005 | Waldhauser et al. | |
| 6,964,205 B2 | 11/2005 | Papakostas et al. | |
| 6,973,339 B2 | 12/2005 | Govari | |
| 6,997,924 B2 | 2/2006 | Schwartz et al. | |
| 7,077,823 B2 | 7/2006 | McDaniel | |
| 7,156,816 B2 | 1/2007 | Schwartz et al. | |
| 7,235,070 B2 | 6/2007 | Vanney | |
| 7,297,116 B2 | 11/2007 | Varghese et al. | |
| 7,306,593 B2 | 12/2007 | Keidar et al. | |
| 7,306,599 B2 | 12/2007 | Karasawa et al. | |
| 7,311,704 B2 | 12/2007 | Paul et al. | |
| 7,397,364 B2 | 7/2008 | Govari | |
| 7,435,232 B2 | 10/2008 | Liebschner | |
| 7,465,288 B2 | 12/2008 | Dudney et al. | |
| 7,481,774 B2 | 1/2009 | Brockway et al. | |
| 7,536,218 B2 | 5/2009 | Govari et al. | |
| 7,604,605 B2 | 10/2009 | Zvuloni | |
| 7,662,151 B2 | 2/2010 | Crompton, Jr. et al. | |
| 7,681,432 B2 | 3/2010 | Hay et al. | |
| 7,686,767 B2 | 3/2010 | Maschke | |
| 7,914,440 B2 | 3/2011 | Otawara | |
| 7,959,601 B2 | 6/2011 | McDaniel et al. | |
| 7,984,659 B2 | 7/2011 | Fujimoto et al. | |
| 8,043,216 B2 | 10/2011 | Matsumura | |
| 8,046,049 B2 | 10/2011 | Govari et al. | |
| 8,083,691 B2 | 12/2011 | Goldenberg et al. | |
| 8,137,275 B2 | 3/2012 | Fan et al. | |
| 8,226,580 B2 | 7/2012 | Govari et al. | |
| 8,333,103 B2 | 12/2012 | Bonyak et al. | |
| 8,357,152 B2 | 1/2013 | Govari et al. | |
| 8,359,082 B2 | 1/2013 | Selkee | |
| 8,374,670 B2 | 2/2013 | Selkee | |
| 8,374,819 B2 | 2/2013 | Govari et al. | |
| 8,380,276 B2 | 2/2013 | Schultz | |
| 8,437,832 B2 | 5/2013 | Govari et al. | |
| 8,521,462 B2 | 8/2013 | Govari et al. | |
| 8,523,787 B2 | 9/2013 | Ludwin et al. | |
| 8,529,476 B2 | 9/2013 | Govari et al. | |
| 8,535,308 B2 | 9/2013 | Govari et al. | |
| 8,731,859 B2 | 5/2014 | Ludwin et al. | |
| 8,818,485 B2 | 8/2014 | Govari et al. | |
| 2001/0047129 A1 | 11/2001 | Hall et al. | |
| 2001/0047133 A1 | 11/2001 | Gilboa et al. | |
| 2002/0002329 A1 | 1/2002 | Avitall | |
| 2002/0065455 A1 | 5/2002 | Ben-Haim et al. | |
| 2002/0068866 A1 | 6/2002 | Zikorus et al. | |
| 2002/0068931 A1 | 6/2002 | Wong et al. | |
| 2002/0165461 A1 | 11/2002 | Hayzelden et al. | |
| 2002/0193781 A1 | 12/2002 | Loeb | |
| 2003/0120150 A1 | 6/2003 | Govari | |
| 2003/0120195 A1 | 6/2003 | Milo et al. | |
| 2003/0130615 A1 | 7/2003 | Tom | |
| 2003/0158494 A1 | 8/2003 | Dahl et al. | |
| 2003/0187389 A1 | 10/2003 | Morency et al. | |
| 2004/0049255 A1 | 3/2004 | Jain et al. | |
| 2004/0064024 A1 | 4/2004 | Sommer | |
| 2004/0068178 A1 | 4/2004 | Govari | |
| 2004/0097806 A1 | 5/2004 | Hunter et al. | |
| 2004/0102769 A1 | 5/2004 | Schwartz et al. | |
| 2004/0147920 A1 | 7/2004 | Keidar | |
| 2004/0244464 A1 | 12/2004 | Hajdukiewicz et al. | |
| 2004/0254458 A1 | 12/2004 | Govari | |
| 2005/0033135 A1 | 2/2005 | Govari | |
| 2005/0080429 A1 | 4/2005 | Freyman et al. | |
| 2005/0096590 A1 | 5/2005 | Gullickson et al. | |
| 2005/0228274 A1 | 10/2005 | Boese et al. | |
| 2005/0277875 A1 | 12/2005 | Selkee | |
| 2006/0009690 A1 | 1/2006 | Fuimaono et al. | |
| 2006/0009735 A1 | 1/2006 | Viswanathan et al. | |
| 2006/0015096 A1 | 1/2006 | Hauck et al. | |
| 2006/0064038 A1 | 3/2006 | Omata et al. | |
| 2006/0074297 A1 | 4/2006 | Viswanathan | |
| 2006/0173480 A1 | 8/2006 | Zhang | |
| 2006/0184106 A1 | 8/2006 | McDaniel et al. | |
| 2006/0200049 A1 | 9/2006 | Leo et al. | |
| 2006/0247618 A1 | 11/2006 | Kaplan et al. | |
| 2007/0060832 A1 | 3/2007 | Levin | |
| 2007/0060847 A1 | 3/2007 | Leo et al. | |
| 2007/0100332 A1 | 5/2007 | Paul et al. | |
| 2007/0106114 A1 | 5/2007 | Sugimoto et al. | |
| 2007/0142749 A1 | 6/2007 | Khatib et al. | |
| 2007/0151391 A1 | 7/2007 | Larkin et al. | |
| 2007/0156114 A1 | 7/2007 | Worley et al. | |
| 2007/0161882 A1 | 7/2007 | Pappone | |
| 2007/0167740 A1 | 7/2007 | Grunewald et al. | |
| 2007/0167818 A1 | 7/2007 | Osborn et al. | |
| 2007/0179492 A1 | 8/2007 | Pappone | |
| 2007/0185397 A1 | 8/2007 | Govari et al. | |
| 2007/0191829 A1 | 8/2007 | McGee et al. | |
| 2007/0197939 A1* | 8/2007 | Wallace et al. ............... 600/587 | |
| 2007/0233044 A1 | 10/2007 | Wallace et al. | |
| 2007/0282211 A1 | 12/2007 | Ofek et al. | |
| 2008/0009750 A1 | 1/2008 | Aeby et al. | |
| 2008/0015568 A1 | 1/2008 | Paul et al. | |
| 2008/0051704 A1 | 2/2008 | Patel et al. | |
| 2008/0065111 A1 | 3/2008 | Blumenkranz et al. | |
| 2008/0071267 A1 | 3/2008 | Wang et al. | |

(56) References Cited

U.S. PATENT DOCUMENTS

| | | |
|---|---|---|
| 2008/0077049 A1 | 3/2008 | Hirshman |
| 2008/0146918 A1 | 6/2008 | Magnin et al. |
| 2008/0183075 A1 | 7/2008 | Govari et al. |
| 2008/0200843 A1 | 8/2008 | Williams et al. |
| 2008/0249467 A1 | 10/2008 | Burnett et al. |
| 2008/0249522 A1 | 10/2008 | Pappone et al. |
| 2008/0255540 A1 | 10/2008 | Selkee |
| 2008/0269606 A1 | 10/2008 | Matsummura |
| 2008/0275428 A1 | 11/2008 | Tegg et al. |
| 2008/0275442 A1 | 11/2008 | Paul et al. |
| 2008/0275465 A1 | 11/2008 | Paul et al. |
| 2008/0281319 A1 | 11/2008 | Paul et al. |
| 2008/0287777 A1 | 11/2008 | Li et al. |
| 2008/0288038 A1 | 11/2008 | Paul et al. |
| 2008/0294144 A1 | 11/2008 | Leo et al. |
| 2008/0294158 A1 | 11/2008 | Pappone et al. |
| 2009/0010021 A1 | 1/2009 | Smith et al. |
| 2009/0093806 A1 | 4/2009 | Govari et al. |
| 2009/0138007 A1 | 5/2009 | Govari et al. |
| 2009/0158511 A1 | 6/2009 | Maze et al. |
| 2009/0177111 A1* | 7/2009 | Miller et al. .......... 600/547 |
| 2009/0275966 A1 | 11/2009 | Mitusina |
| 2009/0287118 A1 | 11/2009 | Malek |
| 2009/0294361 A1 | 12/2009 | Larsen |
| 2009/0306515 A1 | 12/2009 | Matsumura |
| 2009/0306650 A1 | 12/2009 | Govari et al. |
| 2010/0063478 A1 | 3/2010 | Selkee |
| 2010/0069921 A1 | 3/2010 | Miller et al. |
| 2010/0121138 A1 | 5/2010 | Goldenberg et al. |
| 2010/0137845 A1 | 6/2010 | Ramstein et al. |
| 2010/0152574 A1 | 6/2010 | Erdman et al. |
| 2010/0160770 A1 | 6/2010 | Govari et al. |
| 2010/0160778 A1 | 6/2010 | Eskandari et al. |
| 2010/0168620 A1 | 7/2010 | Klimovitch et al. |
| 2010/0168918 A1 | 7/2010 | Zhao et al. |
| 2010/0292566 A1 | 11/2010 | Nagano et al. |
| 2010/0298826 A1* | 11/2010 | Leo et al. .......... 606/41 |
| 2011/0054354 A1 | 3/2011 | Hunter et al. |
| 2011/0054355 A1 | 3/2011 | Hunter et al. |
| 2011/0071436 A1 | 3/2011 | Althoefer et al. |
| 2011/0130648 A1 | 6/2011 | Beeckler et al. |
| 2011/0153252 A1 | 6/2011 | Govari et al. |
| 2011/0153253 A1 | 6/2011 | Govari et al. |
| 2011/0160556 A1 | 6/2011 | Govari |
| 2011/0172538 A1 | 7/2011 | Sumi |
| 2011/0184406 A1 | 7/2011 | Selkee |
| 2011/0307207 A1 | 12/2011 | Govari et al. |
| 2012/0004576 A1 | 1/2012 | Govari et al. |
| 2012/0041295 A1 | 2/2012 | Schultz |
| 2012/0089358 A1 | 4/2012 | Ludwin et al. |
| 2012/0108988 A1 | 5/2012 | Ludwin et al. |
| 2012/0149966 A1 | 6/2012 | Ludwin et al. |
| 2012/0149967 A1 | 6/2012 | Ludwin et al. |
| 2012/0150075 A1 | 6/2012 | Ludwin et al. |
| 2012/0184864 A1 | 7/2012 | Harlev et al. |
| 2012/0184865 A1 | 7/2012 | Harlev et al. |
| 2012/0253167 A1 | 10/2012 | Bonyak et al. |
| 2012/0259194 A1 | 10/2012 | Selkee |
| 2012/0271145 A1 | 10/2012 | Govari et al. |
| 2012/0310116 A1 | 12/2012 | Ludwin et al. |
| 2012/0316407 A1 | 12/2012 | Anthony et al. |
| 2013/0018306 A1 | 1/2013 | Ludwin et al. |
| 2013/0096551 A1 | 4/2013 | Govari et al. |
| 2013/0131663 A1 | 5/2013 | Govari et al. |
| 2013/0172875 A1 | 7/2013 | Govari et al. |
| 2014/0024969 A1 | 1/2014 | Govari et al. |
| 2014/0024970 A1 | 1/2014 | Govari et al. |
| 2014/0032152 A1 | 1/2014 | Govari et al. |

FOREIGN PATENT DOCUMENTS

| | | |
|---|---|---|
| EP | 980693 A1 | 2/2000 |
| EP | 1502555 A1 | 2/2005 |
| EP | 1586281 A1 | 10/2005 |
| EP | 1690564 A1 | 8/2006 |
| EP | 1743575 A2 | 1/2007 |
| EP | 1820464 A1 | 8/2007 |
| EP | 1897581 A2 | 3/2008 |
| EP | 2000789 A2 | 12/2008 |
| EP | 2047797 A2 | 4/2009 |
| EP | 2127604 A1 | 12/2009 |
| EP | 2130508 B1 | 12/2009 |
| EP | 2196143 A1 | 6/2010 |
| EP | 2305115 A1 | 4/2011 |
| EP | 2338412 A1 | 6/2011 |
| EP | 2172240 B1 | 12/2012 |
| EP | 2338411 B1 | 11/2013 |
| JP | 8243168 A | 9/1996 |
| JP | 2000126301 A | 5/2000 |
| JP | 2000508224 A | 7/2000 |
| JP | 2005040215 | 2/2005 |
| JP | 2005237964 A | 9/2005 |
| JP | 2005345215 A | 12/2005 |
| JP | 2006064465 A | 3/2006 |
| JP | 2006255401 A | 9/2006 |
| JP | 2007181696 A | 7/2007 |
| WO | WO 94/17856 A1 | 8/1994 |
| WO | WO 95/10326 A | 4/1995 |
| WO | WO 96/05768 A1 | 2/1996 |
| WO | WO 97/29678 A | 8/1997 |
| WO | WO 97/29709 A | 8/1997 |
| WO | WO 97/29710 A | 8/1997 |
| WO | WO 98/29032 A | 7/1998 |
| WO | WO 03/020139 A | 3/2003 |
| WO | WO 2006/029563 A | 3/2006 |
| WO | WO 2006/086152 A | 8/2006 |
| WO | WO 2006/092563 A | 9/2006 |
| WO | WO 2006/135483 A2 | 12/2006 |
| WO | WO 2007/015139 A2 | 2/2007 |
| WO | WO 2007/025230 A | 3/2007 |
| WO | WO 2007/050960 A | 5/2007 |
| WO | WO 2007/067938 A | 6/2007 |
| WO | WO 2007/076312 A2 | 7/2007 |
| WO | WO 2007/082216 A | 7/2007 |
| WO | WO 2007/098494 A1 | 8/2007 |
| WO | WO 2007/111182 A | 10/2007 |
| WO | WO 2008/053402 A1 | 5/2008 |
| WO | WO 2008/147599 A1 | 12/2008 |
| WO | WO 2009/065140 A1 | 5/2009 |
| WO | WO 2009/078280 A | 6/2009 |
| WO | WO 2009/085470 A | 7/2009 |
| WO | WO 2009/147399 A | 12/2009 |
| WO | WO 2010/008975 A | 1/2010 |
| WO | WO 2011/046874 A1 | 4/2011 |

OTHER PUBLICATIONS

Biter, William J. et al., "Magnetic Wire for Monitoring Strain in Composites", *Sensors*, Jun. 2001, www.sensormag.com, pp. 110-114.

Guo, Shuxiang et al., "Control and Experimental results of a Catheter Operating System", Feb. 21-26, 2009, Proceedings of the 2008 IEEE, International Conference on Robotics and Biomimetics, Bankok, Thailand, pp. 91-95.

Instron Marketing Brochure, "Medical Device Testing Systems", Instron 2007 http://web.archive.org/web/20080318092822/http://www.instron.com.tr/wa/library/streamfile.aspx?doc=1678&downland=true.

Instron, "Series 3300 Load Frames, Reference Manual Equipment", Instron, pp. 1-5 and 1-10, 2004.

Kanagaratnam, Prapa et. al., "Experience of robotic catheter ablation in humans using novel remotely steerable catheter sheath", Journal of Interventional Cardiac Electrophysiology. vol. 21, No. 1, p. 19-26 (2008).

Okumura, M.D. Yasuo et al. "A Systematic Analysis of In Vivo Contact Forces on Virtual Catheter Tip/Tissue Surface Contact during Cardiac Mapping and Intervention", Journal of Cardiovascular Electrophysiology, Jun. 2008, pp. 632-640, vol. 19, No. 6.

Peirs, J. et al., "Design of an Optical Force Sensor for Force Feedback during Minimally Invasive Robotic Surgery", Eurosensors XVII, (56) References Cited

OTHER PUBLICATIONS 2003, pp. 1063-1066, http://mech.kuleuven.be/micro/pub/medic/Paper_Eurosensors_2003_MIS_sensor_extended.pdf.
Partial European Search Report mailed on Sep. 18, 2009 from related European Patent Application No. 08253265.6.
Partial European Search Report mailed on Dec. 7, 2009 from related European Patent Application No. 09251502.2.
European Search Report mailed on Mar. 8, 2010 from related European Patent Application No. 09252143.4.
Partial European Search Report mailed on Mar. 29, 2010 from related European Patent Application No. 09252879.3.
Partial European Search Report mailed on Apr. 1, 2010 from related European Patent Application No. 09252721.7.
European Search Report mailed on Mar. 2, 2011 from related European Patent Application No. 10175931.4.
European Search Report mailed on Mar. 28, 2011 from related European Patent Application No. 10252189.5.
European Search Report mailed on Mar. 28, 2011 from related European Patent Application No. 10252191.1.
European Search Report mailed on Mar. 30, 2011 from related European Patent Application No. 10252020.2.
European Search Report mailed on May 16, 2011 from related European Patent Application No. 10252232.3.
European Search Report mailed on Aug. 5, 2011 from related European Patent Application No. 11158804.2.
European Search Report mailed on Sep. 20, 2011 from related European Patent Application No. 11250066.5.
European Search Report mailed on Sep. 23, 2011 from related European Patent Application No. 11169251.3.
European Search Report mailed on Oct. 28, 2011 from related European Patent Application No. 11171842.5.
European Search Report mailed on Nov. 17, 2011 from related European Patent Application No. 11177600.1.
European Search Report mailed on Feb. 15, 2012 from related European Patent Application No. 11182854.7.
European Search Report mailed on May 2, 2012 from related European Patent Application No. 11189326.9.
European Search Report mailed on Jun. 4, 2012 from related European Patent Application No. 12163784.7.
European Search Report mailed on Jul. 20, 2012 from related European Patent Application No. 12161784.9.
European Search Report mailed on Nov. 20, 2012 from related European Patent Application No. 12176163.9.
European Search Report mailed on Feb. 11, 2013 from corresponding European Patent Application No. 11187525.8.
European Search Report mailed on Apr. 9, 2013 from related European Patent Application No. 13150145.4.

\* cited by examiner

ZERO-DRIFT DETECTION AND CORRECTION IN CONTACT FORCE MEASUREMENTS

FIELD OF THE INVENTION

The present invention relates generally to invasive probes, and specifically to calibrating force sensors in invasive probes.

BACKGROUND OF THE INVENTION

A wide range of medical procedures involve placing objects, such as sensors, tubes, catheters, dispensing devices and implants, within a patient's body. Position sensing systems have been developed for tracking such objects. Magnetic position sensing is one of the methods known in the art. In magnetic position sensing, magnetic field generators are typically placed at known positions external to the patient. A magnetic field sensor within the distal end of a probe generates electrical signals in response to these magnetic fields, which are processed in order to determine the position coordinates of the distal end of the probe. These methods and systems are described in U.S. Pat. Nos. 5,391,199, 6,690,963, 6,484,118, 6,239,724, 6,618,612 and 6,332,089, in PCT International Publication WO 1996/005768, and in U.S. Patent Application Publications 2002/0065455 A1, 2003/0120150 A1 and 2004/0068178 A1, whose disclosures are all incorporated herein by reference.

When placing a probe within the body, it may be desirable to have the distal tip of the probe in direct contact with body tissue. The contact can be verified, for example, by measuring the contact pressure between the distal tip and the body tissue. U.S. Patent Application Publications 2007/0100332, 2009/0093806 and 2009/0138007, whose disclosures are incorporated herein by reference, describe methods of sensing contact pressure between the distal tip of a catheter and tissue in a body cavity using a force sensor embedded in the catheter.

SUMMARY OF THE INVENTION

An embodiment of the present invention provides a method, including:

inserting a probe having a force sensor into a body cavity of a patient;

receiving from the force sensor a plurality of measurements, each of the measurements indicative of a force applied to the force sensor;

detecting that the measurements received over a period of time of at least a specified duration have not varied by more than a predefined amount; and setting a baseline of the force sensor, for use in further measurements, to a value based on the measurements received during the period.

Typically, the probe includes a cardiac catheter.

In one embodiment the body cavity includes a chamber of a heart.

The method may include:

applying a filter to the measurements upon detecting that the measurements have not varied by more than the predefined amount, the filter being configured to isolate filtered measurements within a specific frequency range; and setting the baseline upon detecting that the filtered measurements do not indicate contact between the probe and the body cavity tissue.

Typically, setting the baseline includes calculating a function based on the received measurements. The function may be an average of the received measurements.

In a disclosed embodiment the specified duration includes at least a single cardiac cycle.

In an alternative embodiment the predefined amount is greater than a noise variation of the force sensor.

In a further alternative embodiment the method includes evaluating the force applied by a distal tip of the probe to a surface of the body cavity by subtracting the baseline from the received measurements, upon detecting that the received measurements vary by more than the predefined amount.

There is further provided, according to another embodiment of the present invention, apparatus, including:

a probe, configured for insertion into a body cavity of a patient and including a force sensor for measuring a force applied to the force sensor; and a processor, which is configured to receive a plurality of measurements from the force sensor, each of the measurements indicative of the force, to detect that the measurements received over a period of time of at least a specified duration have not varied by more than a predefined amount, and to set a baseline of the force sensor, for use in further measurements, to a value based on the measurements received during the period.

There is further provided, according to another embodiment of the present invention, a computer software product, operated in conjunction with a medical probe that includes a force sensor for measuring a force applied to the force sensor, the product including a non-transitory computer-readable medium, in which program instructions are stored, which instructions, when read by a computer, cause the computer to receive a plurality of measurements from the force sensor, each of the measurements indicative of the force, to detect that the measurements received over a period of time of at least a specified duration have not varied by more than a predefined amount, and to set a baseline of the force sensor, for use in further measurements, to a value based on the measurements received during the period.

BRIEF DESCRIPTION OF THE DRAWINGS

The disclosure is herein described, by way of example only, with reference to the accompanying drawings, wherein.

DETAILED DESCRIPTION OF EMBODIMENTS

Overview

Various diagnostic and therapeutic procedures, such as cardiac ablation and intracardiac electrical mapping, use an invasive probe, such as a catheter, whose distal tip is fitted with at least one electrode. The electrode is typically operated when the probe is pressed against a body cavity surface. In these procedures, it is usually important to ascertain a force the distal tip is exerting on the body cavity surface. Therefore, some catheters comprise force sensors for measuring the force between the probe and intra-body tissue, such as the endocardium.

To accurately measure a force exerted by the distal tip on the endocardium, the force sensor is typically calibrated to a "zero level," also referred to herein as a baseline. In embodiments of the present invention, the baseline is determined from measurements generated by the force sensor when the distal tip has minimal contact with any surface (and therefore there is essentially no effective force exerted on the distal tip). Once the baseline is identified, the measurements from the force sensor can be used to provide a value of the force exerted.

Since force sensors in catheters typically rely on analog components, the sensors are susceptible to a "baseline drift," where the baseline may change due to factors including, but not limited to, temperature and aging (i.e., of the analog components). The baseline drift may result in an incorrect zero level of the force sensor, thereby introducing inaccuracy into the evaluated forces when the distal tip engages the intra-body tissue. In order to ensure accurate force values, embodiments of the present invention provide methods and systems for detecting and correcting the baseline drift of a force sensor disposed in a catheter. In some embodiments, the measurements from the force sensor are monitored during an intracardiac procedure (i.e., while the catheter is inside a heart of a patient). During the procedure, upon detecting that the measurements are within a predefined noise threshold (i.e., the measurements are relatively stable) for a specified duration, then the catheter is assumed to be out of contact with the endocardial tissue, and a current baseline is calculated using the measurements collected during the specified duration.

On the other hand, when the measurements vary by more than the predetermined noise threshold, the catheter may be assumed to be in contact with the endocardial tissue. The measurements received in these cases, i.e., when the measurements vary, may be used to give a value of the force exerted on the sensor.

Embodiments of the present invention enable automatic calibration of a force sensor in a dynamic system. In some embodiments the force sensor can be automatically recalibrated whenever a change is detected in the baseline, even if the change is detected during an intracardiac procedure. Detecting and correcting the baseline drift in the force sensor enables a catheterization system to measure force with improved accuracy and reliability.

System Description

Figure 1:
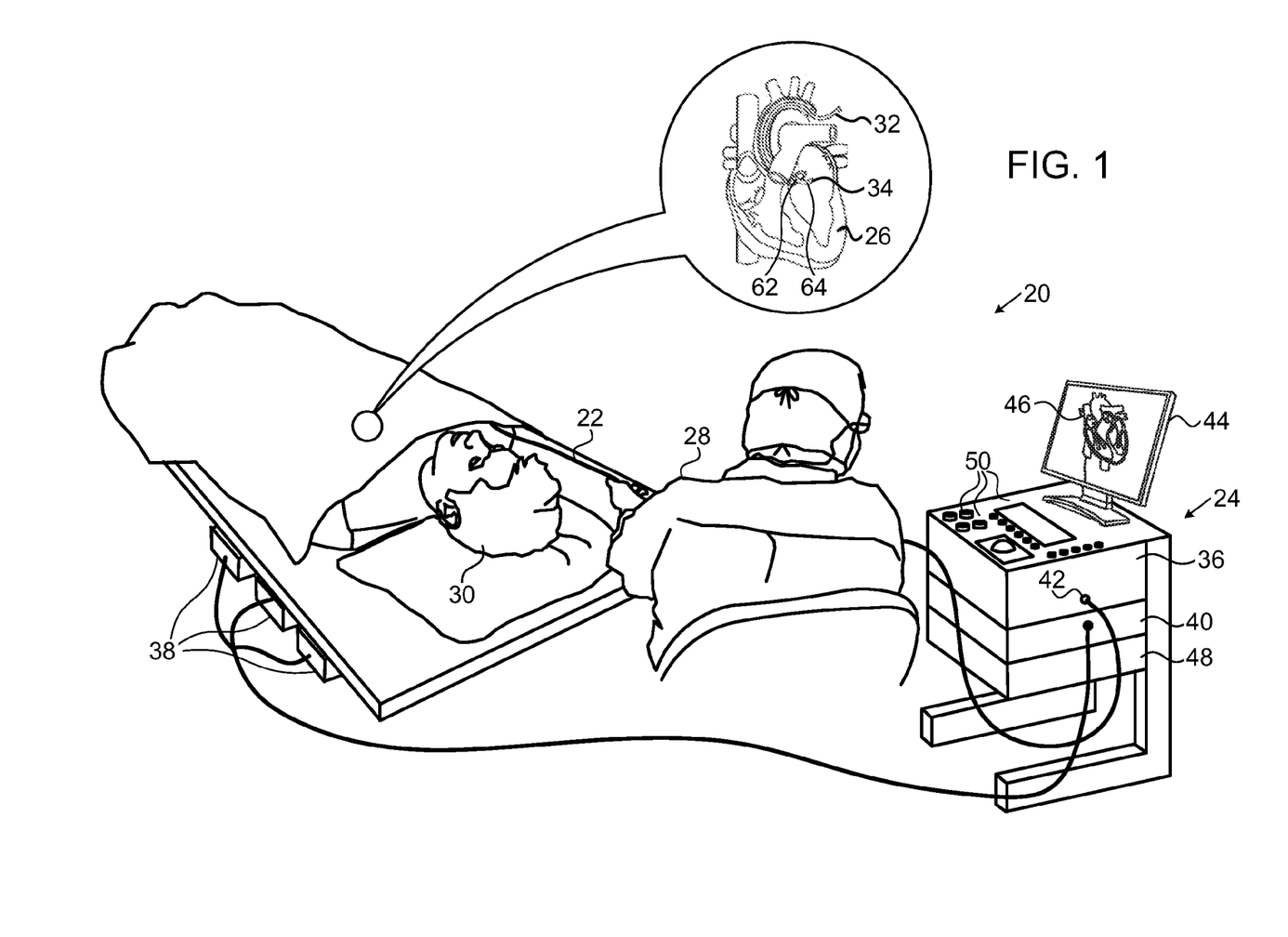
FIG. 1 is a schematic pictorial illustration of a zero-drift detection and correction system for a pressure-sensitive catheter, in accordance with an embodiment of the present invention.

FIG. 1 is an illustration of a medical system 20 that uses zero-drift detection and correction, in accordance with an embodiment of the invention. System 20 may be based, for example, on the CARTO™ system, produced by Biosense Webster Inc. (Diamond Bar, Calif.). System 20 comprises a probe 22, such as a catheter, and a control console 24. In the embodiment described hereinbelow, it is assumed that probe 22 is used for diagnostic or therapeutic treatment, such as for mapping electrical potentials in a heart 26 or performing ablation of heart tissue. Alternatively, probe 22 may be used, mutatis mutandis, for other therapeutic and/or diagnostic purposes in the heart or in other body organs.

An operator 28, such as a cardiologist, inserts probe 22 through the vascular system of a patient 30 so that a distal end 32 of probe 22 enters a chamber of heart 26. Operator 28 advances probe 22 so that a distal tip 34 of probe 22 engages endocardial tissue at a desired location or locations. Probe 22 is typically connected by a suitable connector at its proximal end to console 24.

Console 24 typically uses magnetic position sensing to determine position coordinates of distal end 32 inside heart 26. To determine the position coordinates, a driver circuit 36 in console 24 drives field generators 38 to generate magnetic fields within the body of patient 30. Typically, field generators 38 comprise coils, which are placed below the patient's torso at known positions external to patient 30. These coils generate magnetic fields in a predefined working volume that contains heart 26. A magnetic field sensor 62 within distal end 32 of probe 22 (sensor 62 is shown in more detail in FIG. 2) generates electrical signals in response to these magnetic fields. A signal processor 40 processes these signals in order to determine the position coordinates of distal end 32, typically including both location and orientation coordinates. The method of position sensing described hereinabove is implemented in the above-mentioned CARTO™ system and is described in detail in the patents and patent applications cited above.

Signal processor 40 typically comprises a general-purpose computer, with suitable front end and interface circuits for receiving signals from probe 22 and controlling the other components of console 24. Processor 40 may be programmed in software to carry out the functions that are described herein. The software may be downloaded to console 24 in electronic form, over a network, for example, or it may be provided on non-transitory tangible media, such as optical, magnetic or electronic memory media. Alternatively, some or all of the functions of processor 40 may be carried out by dedicated or programmable digital hardware components.

An input/output (I/O) interface 42 enables console 24 to interact with probe 22. Based on the signals received from probe 22 (via interface 42 and other components of system 20), processor 40 drives a display 44 to present operator 30 with an image 46 showing the position of distal end 32 in the patient's body, as well as status information and guidance regarding the procedure that is in progress.

In the present embodiment, processor 40 monitors the signal measurements received from a force sensor 64 within distal end 32 (force sensor 64 is shown in more detail in FIG. 2) during periods in which the catheter is believed to be out of contact with the endocardium, and detects any baseline drift. If a baseline drift is detected, processor 40 can correct the signals from the force sensor when distal tip 34 engages the endocardial tissue, in order to make an accurate evaluation of the force experienced by the sensor.

Processor 40 stores data representing image 46 in a memory 48. In some embodiments, operator 28 can manipulate image 46 using one or more input devices 50.

Alternatively or additionally, system 20 may comprise an automated mechanism (not shown) for maneuvering and operating probe 22 within the body of patient 30. Such mechanisms are typically capable of controlling both the longitudinal motion (advance/retract) of probe 22 and transverse motion (deflection/steering) of distal end 32 of the probe. In such embodiments, processor 40 generates a control input for controlling the motion of probe 22 based on the signals provided by the magnetic field sensor in the probe.

Although FIG. 1 shows a particular system configuration, other system configurations can also be employed to implement embodiments of the present invention, and are thus considered to be within the spirit and scope of this invention. For example, the methods described hereinbelow may be applied using position transducers of types other than the magnetic field sensor described above, such as impedance-based or ultrasonic position sensors. The term "position transducer" as used herein refers to an element mounted on probe 22 which causes console 24 to receive signals indicative of the coordinates of the element. The position transducer may thus comprise a receiver on the probe, which generates a position signal to the control unit based on energy received by the transducer; or it may comprise a transmitter, emitting energy that is sensed by a receiver external to the probe. Furthermore, the methods described hereinbelow may similarly be applied in therapeutic and diagnostic applications using not only catheters, but also probes of other types, both in the heart and in other body organs and regions.

Figure 2:
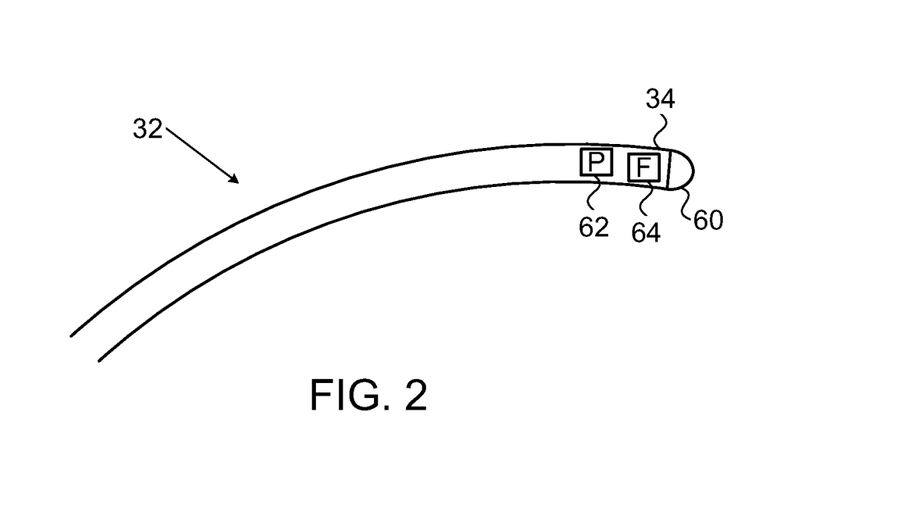
FIG. 2 is a schematic side view showing details of the distal portion of the pressure-sensitive catheter, in accordance with an embodiment of the present invention.

FIG. 2 is a schematic sectional view of distal end 32 of probe 22, in accordance with an embodiment of the present invention. Specifically, FIG. 2 shows functional elements of distal end 32 used for therapeutic and/or diagnostic activity. An electrode 60 (e.g., an ablation electrode) at distal tip 34 of the probe is typically made of a metallic material, such as a platinum/iridium alloy or another suitable material. Alternatively, multiple electrodes (not shown) along the length of the probe may be used for this purpose.

Position sensor 62 transmits a signal to console 24 that is indicative of the location coordinates of distal end 32. Position sensor 62 may comprise one or more miniature coils, and typically comprises multiple coils oriented along different axes. Alternatively, position sensor 62 may comprise either another type of magnetic sensor, an electrode which serves as a position transducer, or position transducers of other types, such as impedance-based or ultrasonic position sensors. Although FIG. 2 shows a probe with a single position sensor, embodiments of the present invention may utilize probes with more than one position sensor.

In an alternative embodiment, the roles of position sensor 62 and magnetic field generators 38 may be reversed. In other words, driver circuit 36 may drive a magnetic field generator in distal end 32 to generate one or more magnetic fields. The coils in generator 38 may be configured to sense the fields and generate signals indicative of the amplitudes of the components of these magnetic fields. Processor 40 receives and processes these signals in order to determine the position coordinates of distal end 32 within heart 26.

Force sensor 64 measures a force applied by distal tip 34 to the endocardial tissue of heart 26 by conveying a signal to the console that is indicative of the force exerted by the distal tip on the intra-body tissue. In one embodiment, the force sensor may comprise a magnetic field transmitter and receiver connected by a spring in distal end 32, and may generate an indication of the force based on measuring the deflection of the spring. Further details of this sort of probe and force sensor are described in U.S. Patent Application Publications 2009/0093806 and 2009/0138007, whose disclosures are incorporated herein by reference. Alternatively, distal end 32 may comprise another type of force sensor.

Zero-Drift Detection and Correction

Figure 3:
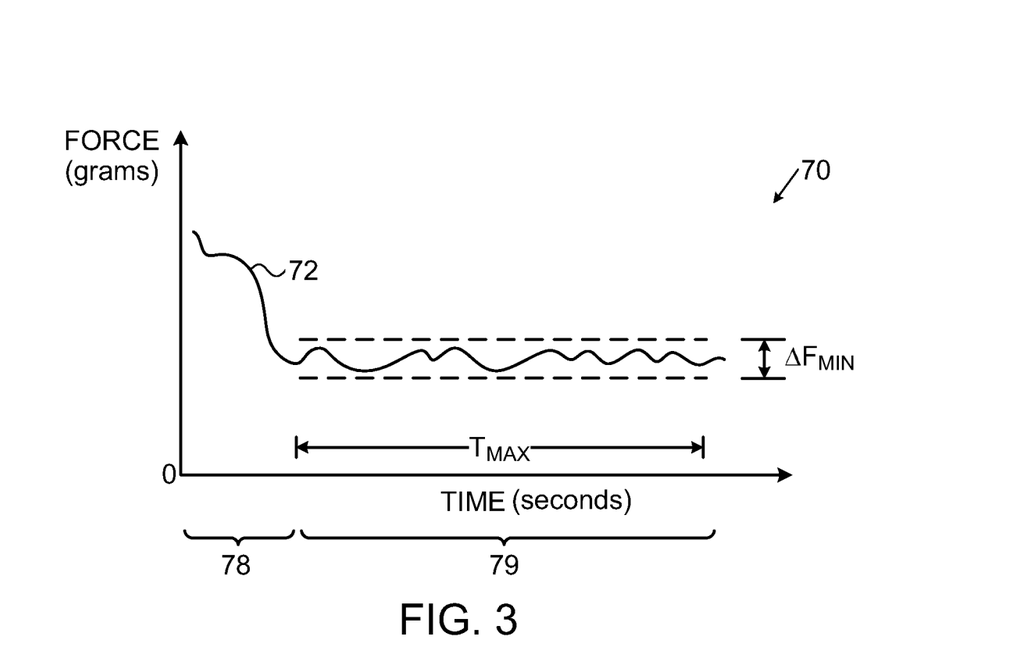
FIG. 3 is a graph showing zero-drift of the pressure sensitive catheter in accordance with an embodiment of the present invention.

FIG. 3 is a graph 70 plotting force (in grams) vs. time (in seconds) for a signal 72 comprising measurements transmitted by force sensor 64 during an intracardiac procedure, in accordance with an embodiment of the present invention. When signal 72 is within a noise threshold $\Delta F_{min}$ over a specified duration $T_{max}$, distal tip 34 may be assumed to be out of contact with the endocardial tissue. On the other hand, when signal 72 varies by more than $\Delta F_{min}$, distal tip 34 may be assumed to be in contact with the endocardial tissue.

Noise threshold $\Delta F_{min}$ is typically set to a value greater then a noise variation for force sensor 64. For example, $\Delta F_{min}$ may be set to 3.0 grams if force sensor 64 has a noise variation of 1.0 grams. In one embodiment, by way of example, the value of $\Delta F_{min}$ is set to be equal to $\pm 3\sigma$, where $\sigma$ is the standard deviation of the signal from sensor 64 when it is out of contact with tissue. Those having ordinary skill in the art will be able to define values of other noise thresholds, such as $\pm n\sigma$ where n is a real number, or a threshold based on a peak-peak variation, without undue experimentation, and all such thresholds are assumed to be comprised within the scope of the present invention.

In one embodiment $T_{max}$ may be set to 2.5 seconds, which is substantially longer than a single cardiac cycle for heart 26 (a cardiac cycle is typically less than or equal to 1.0 seconds).

During a time period 78, signal 72 varies outside the range defined by $\Delta F_{min}$ (due to movement of heart 26), indicating that distal tip 34 is probably in contact with the endocardial tissue. However, during a time period 79 (equal to $T_{max}$ in the example shown in graph 70), signal 72 varies within $\Delta F_{min}$, indicating that distal tip 34 is probably out of contact with the endocardial tissue. The variation of the signal, during a period $T_{max}$, by an amount less than or equal to $\Delta F_{min}$, is indicative that there is effectively no force on sensor 64 during this period. The signals acquired during this period may thus be used to formulate a baseline for the sensor, as is explained in more detail by the flow diagram of FIG. 4.

In some embodiments, there may be tissue contact even when signal 72 has a variation equal to or less than $\Delta F_{min}$. To verify tissue contact when signal 72 has a variation equal to or less than $\Delta F_{min}$, processor 40 may apply a filter to isolate particular frequencies of signal 72. The filter, typically a band-pass filter, is configured to pass signals whose frequency approximates heart rate frequencies (i.e., in this case the frequency of heart 26), and block other frequencies. The band-pass filter can provide a more accurate analysis of signal 72 when distal tip 34 is in low level contact with a moving object such as the endocardial tissue, by allowing comparison between a level of the filtered signal with a predefined level of the band-pass frequencies.

Figure 4:
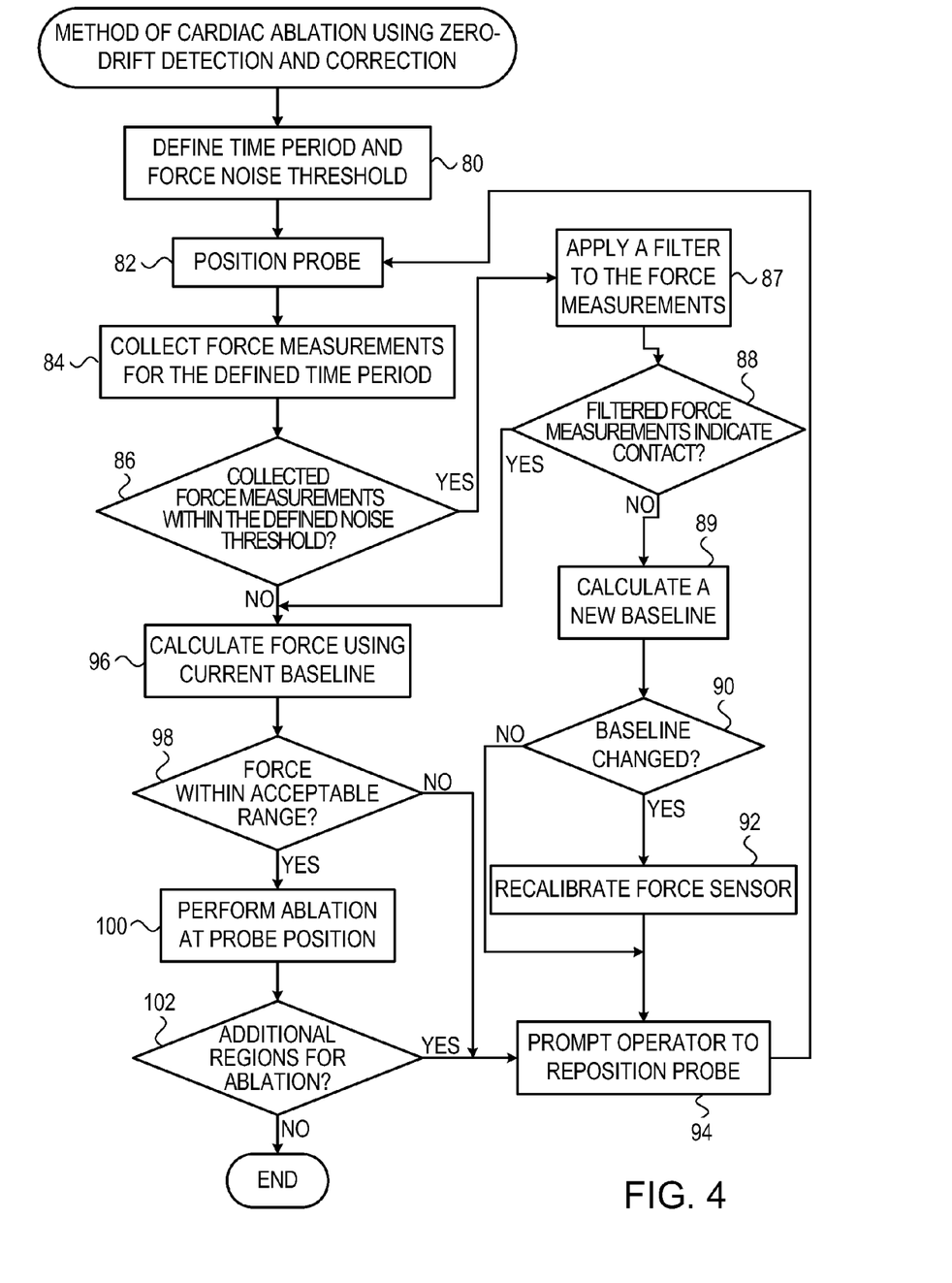
FIG. 4 is a flow diagram that schematically illustrates a method of zero-drift detection and correction for the pressure-sensitive catheter, in accordance with an embodiment of the present invention.

FIG. 4 is a flow diagram that schematically illustrates a method of cardiac ablation using zero-drift detection and correction, in accordance with an embodiment of the present invention. It will be understood that the flow diagram is presented by way of example, and that embodiments of the present invention are not limited to procedures involving cardiac ablation. Rather, embodiments of the present invention may be used wherever the baseline of a force sensor is to be determined while the sensor is operating within a body.

In an initial step 80, operator 30 using input devices 50, sets the noise threshold $\Delta F_{min}$, the specified duration $T_{max}$, and the predefined level of the band-pass frequencies referred to above. Alternatively, $\Delta F_{min}$, $T_{max}$ and the predefined level may be defined in advance of the ablation procedure, and stored in memory 48.

After operator 30 positions probe 22 in a positioning step 82, processor 40, in a collecting step 84, collects measurements from force sensor 64 for the specified duration $T_{max}$. In a first comparison step 86, if the collected force measurements are within $\Delta F_{min}$, then in a filter step 87, processor 40 applies a band-pass filter to filter the force sensor measurements by isolating measurements within a specific frequency range, as described supra. In a second comparison step 88, if the filtered force measurements do not indicate probe-tissue contact, then the method continues to a baseline calculation step 89. The comparison performed in step 88, to evaluate if contact is or is not indicated, typically comprises a comparison of a level of the filtered force measurements with the predefined level of band-pass frequencies defined in step 80. In baseline calculation step 89, processor 40 calculates a new baseline by averaging the collected force measurements (i.e., those that were collected during the specified duration). Alternatively, processor 40 may calculate an alternative function based on the collected force measurements to determine the new baseline.

In a third comparison step 90, if the new baseline differs from a baseline currently associated with force sensor 64 (i.e., a previous baseline), then processor 40, in a recalibration step 92, recalibrates force sensor 64 by setting the zero level of the force sensor to the new baseline, and the processor may present a notification on display 44 informing operator 28 of the automatic baseline change. Alternatively, the processor may present a message on display 44 notifying operator 28 of a baseline change. In this case the operator may be provided with the option of retaining the previous baseline, or of implementing the new baseline. The new baseline may be implemented during later contact with the endocardial tissue.

After recalibrating force sensor 64, processor 40, in a prompting step 94, presents a notification on display 44 that operator 28 may reposition probe 22, and the method returns to step 82. Returning to step 90, if the baseline did not change, then the method continues with step 94.

Returning to steps 86 and 88, if either the collected force measurements exceed $\Delta F_{min}$ (i.e., the collected measurements varied by more than the predefined amount $\Delta F_{min}$ in step 86) or the filtered force measurements indicate probe-tissue contact (in step 88), then distal tip 34 is assumed to be experiencing a non-zero force, typically because it is in contact with the endocardial tissue (or another surface of a body cavity) and the method proceeds to a force calculation step 96. In step 96, processor 40 subtracts the current baseline from the measurements collected from force sensor 64 (i.e., during contact between distal tip 34 and the endocardial tissue), thereby providing an accurate measurement of the force that distal tip 34 is exerting on the endocardial tissue. In some embodiments, processor 40 may present a notification on display 44 warning operator 28 not to implement calculation of a new baseline when distal tip 34 is assumed to be experiencing a non-zero force (e.g., during time period 78).

In a fourth comparison step 98, if the calculated force is within a defined range acceptable for ablation, then in an ablation step 100, processor 40 presents a notification on display 44 prompting operator 28 to perform an ablation at the current probe position. Returning to step 98, if the calculated force is not within the defined range, the method continues with step 94. Finally, in a fifth comparison step 102, if there are additional regions in heart 26 targeted for ablation, the method continues with step 94 until the ablation procedure is complete.

The corresponding structures, materials, acts, and equivalents of all means or steps plus function elements in the claims below are intended to include any structure, material, or act for performing the function in combination with other claimed elements as specifically claimed. The description of the present disclosure has been presented for purposes of illustration and description, but is not intended to be exhaustive or limiting to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method, comprising:
    inserting a probe having a force sensor into a body cavity of a patient;
    receiving from the force sensor a plurality of measurements, each of the measurements indicative of a force applied to the force sensor;
    detecting that the measurements received over a period of time of at least a specified duration have not varied by more than a predefined amount; and
    automatically setting a baseline of the force sensor in a dynamic system, for use in further measurements, to a value based on the measurements received during the period.

2. The method according to claim 1, wherein the probe comprises a cardiac catheter.

3. The method according to claim 1, wherein the body cavity comprises a chamber of a heart.

4. The method according to claim 1, and comprising:
    applying a filter to the measurements upon detecting that the measurements have not varied by more than the predefined amount, the filter being configured to isolate filtered measurements within a specific frequency range; and
    setting the baseline upon detecting that the filtered measurements do not indicate contact between the probe and the body cavity tissue.

5. The method according to claim 1, wherein setting the baseline comprises calculating a function based on the received measurements.

6. The method according to claim 5, wherein the function comprises an average of the received measurements.

7. The method according to claim 1, wherein the specified duration comprises at least a single cardiac cycle.

8. The method according to claim 1, wherein the predefined amount is greater than a noise variation of the force sensor.

9. The method according to claim 1, and comprising evaluating the force applied by a distal tip of the probe to a surface of the body cavity by subtracting the baseline from the received measurements, upon detecting that the received measurements vary by more than the predefined amount.

10. An apparatus, comprising:
    a probe, configured for insertion into a body cavity of a patient and comprising a force sensor for measuring a force applied to the force sensor; and
    a processor, which is configured to receive a plurality of measurements from the force sensor, each of the measurements indicative of the force, to detect that the measurements received over a period of time of at least a specified duration have not varied by more than a predefined amount, and to automatically set a baseline of the force sensor in a dynamic system, for use in further measurements, to a value based on the measurements received during the period.

11. The apparatus according to claim 10, wherein the probe comprises a cardiac catheter.

12. The apparatus according to claim 10, wherein the body cavity comprises a chamber of a heart.

13. The apparatus according to claim 10, wherein the processor is configured to apply a filter to the measurements upon detecting that the measurements have not varied by more than the predefined amount, the filter being configured to isolate filtered measurements within a specific frequency range, and to set the baseline upon detecting that the filtered measurements do not indicate contact between the probe and the body cavity tissue.

14. The apparatus according to claim 13, wherein the filter comprises a band-pass filter.

15. The apparatus according to claim 10, wherein the processor is configured to set the baseline by calculating a function based on the received measurements.

16. The apparatus according to claim 15, wherein the function comprises an average of the received measurements.

17. The apparatus according to claim 10, wherein the specified duration comprises at least a single cardiac cycle.

18. The apparatus according to claim 10, wherein the predefined amount is greater than a noise variation of the force sensor.

19. The apparatus according to claim 10, wherein the processor is configured to evaluate the force applied by a distal tip of the probe to a surface of the body cavity by subtracting the baseline from the received measurements, upon detecting that the received measurements vary by more than the predefined amount.

20. A computer software product, operated in conjunction with a medical probe that includes a force sensor for measuring a force applied to the force sensor, the product comprising a non-transitory computer-readable medium, in which program instructions are stored, which instructions, when read by a computer, cause the computer to receive a plurality of measurements from the force sensor, each of the measurements indicative of the force, to detect that the measurements received over a period of time of at least a specified duration have not varied by more than a predefined amount, and to automatically set a baseline of the force sensor in a dynamic system, for use in further measurements, to a value based on the measurements received during the period.

* * * * *